(12) United States Patent
Bang

(10) Patent No.: US 8,852,949 B2
(45) Date of Patent: Oct. 7, 2014

(54) UREA SOLUTION QUALITY DETERMINING SYSTEM

(71) Applicant: Hyundai Motor Company, Seoul (KR)

(72) Inventor: Sung-Hoon Bang, Hwaseong-si (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 13/974,463

(22) Filed: Aug. 23, 2013

(65) Prior Publication Data

US 2014/0154814 A1 Jun. 5, 2014

(30) Foreign Application Priority Data

Dec. 5, 2012 (KR) .................. 10-2012-0140606

(51) Int. Cl.
- *F01N 3/00* (2006.01)
- *G01N 31/10* (2006.01)
- *G01N 31/00* (2006.01)

(52) U.S. Cl.
CPC ...................................... *G01N 31/10* (2013.01)
USPC .......................................... 436/108; 436/106

(58) Field of Classification Search
CPC ...... F01N 3/00; F01N 2610/02; F01N 3/2066
USPC .................................................. 436/108, 106
See application file for complete search history.

(56) References Cited

U.S. PATENT DOCUMENTS

| | | | |
|---|---|---|---|
| 2009/0078692 A1* | 3/2009 | Starck | 219/260 |
| 2010/0031641 A1* | 2/2010 | Oda et al. | 60/286 |

* cited by examiner

*Primary Examiner* — Christine T Mui

(74) *Attorney, Agent, or Firm* — Morgan, Lewis & Bockius LLP

(57) ABSTRACT

A urea solution quality determining system may include a urea tank in which a urea solution is filled through a charging hole, a test chamber positioned below the charging hole for holding a portion of the urea solution, a main line connected to the urea tank at a lower part of the urea tank below the test chamber, a test line connected to the test chamber, a pumping line to which the main line and the test line are joined, a pump in the pumping line to pump the urea solution from the test chamber or from the urea tank, a control valve for selectively connecting the main line or the test line to the pumping line, and an injector at an end of the pumping line to inject the urea solution into an exhaust line through which an exhaust gas flows. A method is also described.

5 Claims, 2 Drawing Sheets

UREA SOLUTION QUALITY DETERMINING SYSTEM

CROSS-REFERENCE TO RELATED APPLICATION

The present application claims priority of Korean Patent Application Number 10-2012-0140606 filed Dec. 5, 2012, the entire contents of which application are incorporated herein for all purposes by this reference.

BACKGROUND OF INVENTION

1. Field of Invention

The present invention relates to a urea solution quality determining system for injecting a urea solution on an exhaust line for discharging a nitrogen oxide to reduce the nitrogen oxide and determining quality of the supplied urea solution to cope with the determination result.

2. Description of Related Art

As regulations on an exhaust gas of a vehicle are enhanced, an efficient nitrogen oxide reducing post processing device is required.

A selective catalyst reduction unit has the nitrogen oxide included in the exhaust gas react to ammonia to change the oxide nitrogen into a harmless material. In order to generate ammonia, urea is injected into the exhaust gas.

In particular, in a system for injecting a urea solution, quality of the urea solution is very important. In terms of on-board diagnostics (OBD), a method of sensing the quality of the urea solution to perform warning is required.

The information disclosed in this Background section is only for enhancement of understanding of the general background of the invention and should not be taken as an acknowledgement or any form of suggestion that this information forms the prior art already known to a person skilled in the art.

SUMMARY OF INVENTION

Therefore, various aspects of the present invention are directed to provide a urea solution quality determining system and method for determining that a urea solution is supplied to a urea tank and determining quality of the supplied urea solution to perform warning so that quality of an exhaust gas may be improved and a natural environment may be protected.

A urea solution quality determining system according to various aspects of the present invention may include a urea tank in which a urea solution is filled through an charging hole, a test chamber that is positioned below the charging hole for holding a portion of the urea solution, a main line connected to the urea tank at a lower part of the urea tank below the test chamber, a test line connected to the test chamber, a pumping line into which the main line and the test line are joined, a pump installed in the pumping line to pump the urea solution from the test chamber or from the urea tank, a control valve for selectively connecting the main line or the test line to the pumping line, and an injector disposed at an end of the pumping line to inject the urea solution into an exhaust line through which an exhaust gas flows.

The control valve may be a switch valve installed at a point where the main line and the test line are joined. A selective catalyst reduction unit may be disposed in the exhaust line on a downstream side of the injector. NOx sensors may be disposed on an upstream side and a downstream side of the selective catalyst reduction unit, respectively. A level sensor for sensing a level of the urea solution filled in the urea tank may be disposed in the urea tank.

A urea solution quality determining method according to various aspects of the present invention may include sensing an increase in a urea solution put in a urea tank, determining whether an exhaust amount of a nitrogen oxide included in an exhaust gas is stable, determining whether the urea solution is supplied based on the sensed increase in the urea solution, pumping the urea solution from a test chamber formed below an charging hole of the urea tank to an injector if it is determined that the urea solution is supplied and the exhaust amount of the nitrogen oxide is stable, sensing a reduction rate of a selective catalyst reduction unit while the urea solution is injected from the test chamber, and generating a warning signal if the determined reduction rate of the selective catalyst reduction unit is less than or equal to a set value.

A test line may be connected to the test chamber, a main line may be connected to a lower part of the urea tank, a pumping line into which the main line and the test line are joined may be connected to the injector, a pump may be installed in the pumping line, and a switch valve may be installed at a point where the test line and the main line are joined.

A warning lamp may be lighted in accordance with the warning signal or an output of an engine may be forcibly reduced.

The urea solution quality determining method may further include pumping the urea solution from the urea tank to the injector if the determined reduction rate of the selective catalyst reduction unit exceeds the set value.

As described above, in the urea solution quality determining system of the present invention, when it is determined that the urea solution is supplied, the urea solution put in the test chamber is pumped to the injector through the test line so that the quality of the urea solution may be easily determined.

The methods and apparatuses of the present invention have other features and advantages which will be apparent from or are set forth in more detail in the accompanying drawings, which are incorporated herein, and the following Detailed Description, which together serve to explain certain principles of the present invention.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1:
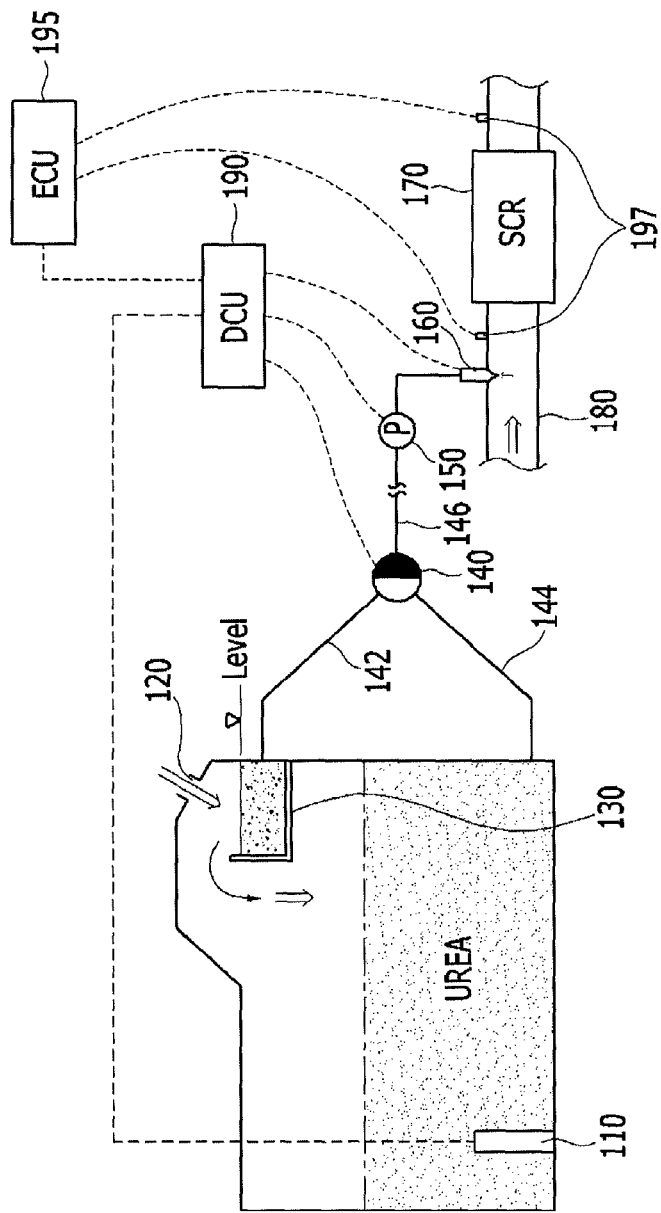
FIG. 1 is a schematic block diagram of an exemplary urea solution quality determining system according to the present invention.

FIG. 1 is a schematic block diagram of a urea solution quality determining system according to various embodiments of the present invention. Referring to FIG. 1, a urea solution quality determining system includes a urea tank 100, a level sensor 110, a test chamber 130, an charging hole 120, a main line 144, a test line 142, a switch valve 140, a pumping line 146, a pump 150, an injector 160, an exhaust line 180, nitrogen oxides (NOx) sensors 197, a selective catalyst reduction unit 170, a dosing control unit 190, and a controller 195.

The charging hole 120 is formed on one upper side of the urea tank 100 and a urea solution is supplied to the charging hole 120. The test chamber 130 is formed below the charging hole 120.

The test chamber 130 is a container that is disposed in the urea tank 100 and in which the urea solution supplied from the charging hole 120 is temporarily put. A bottom and sides of the test chamber 130 are closed and a top of the test chamber 130 is opened.

The urea solution supplied to the charging hole 120 is put in the test chamber 130 and the overflowing urea solution is filled in a lower part of the urea tank 100.

The lower part of the urea tank 100 is connected to the main line 144. The test chamber 130 is connected to the test line 142. The test line 142 and the main line 144 are joined into the pumping line 146.

The switch valve 140 as a control valve is disposed at a point where the main line 144, the test line 142, and the pumping line 146 are joined. The injector 160 is disposed at an end of the pumping line 146. A pump 150 is disposed in the pumping line 146.

The injector 160 injects the urea solution into the exhaust line 180. The selective catalyst reduction unit 170 is disposed on a downstream side of the injector 160.

The NOx sensors 197 are disposed on an upstream side and a downstream side of the selective catalyst reduction unit 170, respectively, to sense a nitrogen oxide included in an exhaust gas and to transmit a sensed signal or signals to the controller 195.

The controller 195 controls the dosing control unit 190 in accordance with the received signal(s) and a driving state of an engine. The dosing control unit 190 controls the switch valve 140, the pump 150, and the injector 160.

By the switch valve 140, the urea solution of the test chamber 130 is pumped to the injector 160 through the test line 142 or the urea solution of the urea tank 100 is pumped to the injector 160 through the main line 144.

The level sensor 110 senses a level of the urea solution filled in the lower part of the urea tank 100 to transmit a sensed signal to the controller 195. The controller 195 determines whether the urea solution is supplied to the urea tank 100 using the signal transmitted by the level sensor 110.

When it is determined that the urea solution is supplied to the urea tank 100 and an exhaust amount of the nitrogen oxide sensed by the NOx sensors 197 is uniform or stable, the pump 150 is operated and the urea solution is injected into the exhaust line 180 through the test chamber 130, the test line 142, the switch valve 140, the pumping line 146, and the injector 160.

Then, the NOx sensors 197 sense the nitrogen oxide included in the exhaust gas after the urea solution is injected. The controller 195 operates a reduction rate of the nitrogen oxide, that is, efficiency of the selective catalyst reduction unit 170.

When it is determined that the efficiency of the selective catalyst reduction unit 170 is lower than or equal to a set value, the controller 195 lights a warning lamp or forcibly reduces an output of the engine.

On the other hand, when it is determined that the efficiency of the selective catalyst reduction unit 170 is higher than the set value, the switch valve 140 is controlled so that the urea solution may be pumped to the injector 160 not through the test line 142 but through the main line 144.

Figure 2:
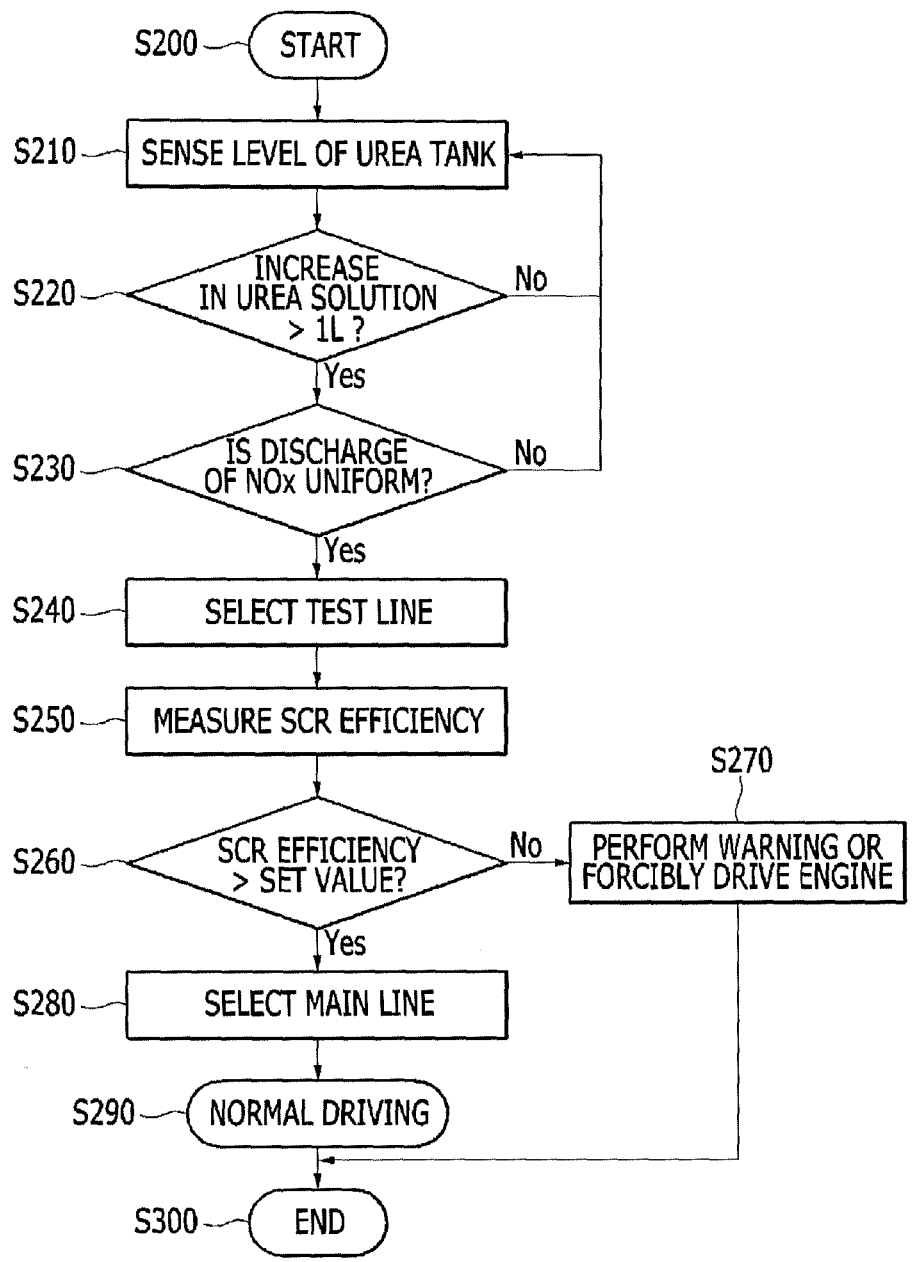
FIG. 2 is a flowchart illustrating an exemplary method of determining quality of a urea solution according to the present invention.

FIG. 2 is a flowchart illustrating a method of determining quality of a urea solution according to various embodiments of the present invention. Referring to FIG. 2, control is started in S200 and a level of the urea tank 100 is sensed in S210. It is determined in S220 whether an increase in the urea solution filled in the urea tank 100 is larger than a set value (e.g., 1 Liter).

It is determined in S230 by the NOx sensors 197 whether an exhaust amount of the nitrogen oxide included in the exhaust gas that passes through the exhaust line 180 is uniform or stable. Here, conditions in which the exhaust amount of the nitrogen oxide is uniform or stable include an idle state in which the engine is uniformly or steadily driven.

When it is determined that the exhaust amount of the nitrogen oxide is uniform or stable, a line through which urea is to be supplied is selected in S240. Here, the test line 142 is selected.

While the urea solution put in the test chamber 130 is injected into the exhaust line 180 through the test line 142 and the injector 160, reduction efficiency of the selective catalyst reduction unit 170 is sensed in S250.

When it is determined in S260 that the reduction efficiency of the selective catalyst reduction unit 170 is lower than a set value, the warning light is lighted or the output of the engine is forcibly reduced in S270.

On the other hand, when it is determined in S260 that the reduction efficiency of the selective catalyst reduction unit 170 is higher than the set value, the urea solution filled in the urea tank 100 is pumped to the injector 160 through the main line 144 instead of the test line 142 in S280. Then, returning to a normal driving mode is performed in S290 and control is terminated in S300.

For convenience in explanation and accurate definition in the appended claims, the terms "upper" or "lower", "upsteam" or "downstream", and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A urea solution quality determining system, comprising:
a urea tank in which a urea solution is filled through a charging hole;
a test chamber that is positioned below the charging hole for holding a portion of the urea solution, wherein the urea tank and the test chamber are not in fluidic communication;
a main line connected to the urea tank at a lower part of the urea tank below the test chamber;
a test line connected to the test chamber;
a pumping line into which the main line and the test line are joined;

a pump installed in the pumping line to pump the urea solution from the test chamber or from the urea tank;

a control valve for selectively connecting the main line or the test line to the pumping line; and an injector disposed at an end of the pumping line to inject the urea solution into an exhaust line through which an exhaust gas flows;

wherein the urea solution of the urea tank or the test chamber is selectively supplied to the injector by operation of the control valve.

2. The urea solution quality determining system of claim 1, wherein the control valve is a switch valve installed at a point where the main line and the test line are joined.

3. The urea solution quality determining system of claim 1, wherein a selective catalyst reduction unit is disposed in the exhaust line on a downstream side of the injector.

4. The urea solution quality determining system of claim 3, wherein NOx sensors are disposed on an upstream side and a downstream side of the selective catalyst reduction unit, respectively.

5. The urea solution quality determining system of claim 1, wherein a level sensor for sensing a level of the urea solution filled in the urea tank is disposed in the urea tank.

* * * * *